United States Patent
Kumar et al.

(10) Patent No.: US 7,135,534 B2
(45) Date of Patent: Nov. 14, 2006

(54) POLYMER SUPPORT FOR SOLID PHASE PEPTIDE SYNTHESIS AND PROCESS FOR PREPARATION THEREOF

(75) Inventors: Gopalakrishnapillai Sankaramangalam Vinod Kumar, Poojappura (IN); Kesavakurup Kumar Santhosh, Poojappura (IN)

(73) Assignees: Rajiv Gandhi Centre for Biotechnology, Kerala (IN); The Secretary, Department of Biotechnology, New Delhi (IN)

( * ) Notice: Subject to any disclaimer, the term of this patent is extended or adjusted under 35 U.S.C. 154(b) by 138 days.

(21) Appl. No.: 10/625,894

(22) Filed: Jul. 24, 2003

(65) Prior Publication Data

US 2005/0020791 A1     Jan. 27, 2005

(51) Int. Cl.
C08F 220/20     (2006.01)
(52) U.S. Cl. .................. 526/320; 526/88; 526/232.1; 526/323.2; 526/347; 525/333.4; 525/333.6; 525/359.3; 525/376

(58) Field of Classification Search ............... 526/320, 526/323.2, 347, 88, 232.1; 525/333.4, 333.6, 525/359.3, 376
See application file for complete search history.

(56) References Cited

U.S. PATENT DOCUMENTS 6,395,842 B1 * 5/2002 Main .................. 525/384

OTHER PUBLICATIONS

Arunan, et al, Solid-Phase Synthesis of a Modified 13-Residue Seminalplasmin Fragment on 1,6-Hexanediol Diacrylate-Crosslinked Polystyrene Support, Peptides (NewYork)(Jun. 2000), 21(6), 773-777.*

* cited by examiner

Primary Examiner—Fred Teskin
(74) Attorney, Agent, or Firm—Venable LLP; Marina V. Schneller

(57) ABSTRACT

A novel polymer support for solid phase peptide synthesis comprising polystyrene backbone and propoxylate function of hexanedioldiacrylate crosslinks having optimum hydrophilic/hydrophobic balance and a process of preparation thereof.

9 Claims, 1 Drawing Sheet

US 7,135,534 B2

Figure 1:
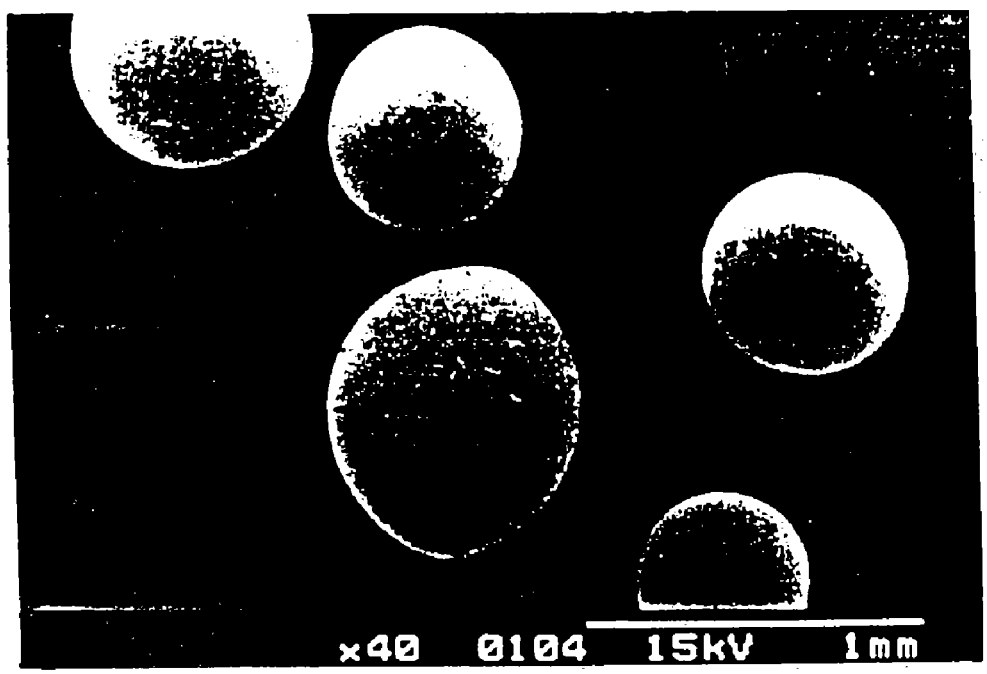

POLYMER SUPPORT FOR SOLID PHASE PEPTIDE SYNTHESIS AND PROCESS FOR PREPARATION THEREOF

BACKGROUND OF THE INVENTION

Peptides play a key role as structural and functional elements in biochemistry/pharmacology and immunology. The fascination with the development of solid phase peptide synthesis (SPPS) stimulated considerable research towards the development of new methodologies, strategies and tactics in peptide synthesis. The efficiency of polymeric support is still a prior suspect in solid phase peptide synthesis. The success of peptide bond formation depends to some extent on the macromolecular characteristics of the crosslinked polymer support used. During the last two decades, several attempts were made to develop hydrophilic supports instead of the rigid, hydrophobic Merrifield resin. The systematic and quantitative research leads to the development of some hydrophilic flexible polymer supports, which show optimum characteristics in solid phase reactions, especially in solid phase peptide synthesis.

Synthesis of biologically active proteins and peptide sequences is significant in revealing the structure-activity correlation and to establish their conformation pattern. The solid phase peptide synthesis reported by Merrifield has made an inestimable contribution to the synthesis of biologically and medicinally important polypeptides.

As the peptide chain grows on the polymer support, its physiochemical properties influence the solvation characteristics of the peptide-bearing support. Therefore, a more ideal support would be one in which the physiochemical characteristics of the support resembles those of the growing peptide chain.

Thus Sheppard and coworkers introduced the polar polyacrylamide based supports. But these supports swell only in polar solvents like dimethylformamide (DMF), dimethylacetamide (DMA) etc. A more compromising situation would be the supports, which are amphiphilic in nature, i.e., which swell in both the polar, and the non-polar solvents employed in peptide synthesis.

Since Merrifield's original report over three decades ago describing solid phase synthesis of a simple tetra peptide on low crosslinked polystyrene beads, the approach has been improved and generalized to the synthesis of complicated peptides, long oligonucleotides and a myriad of small organic molecules. The success of such efforts is often affected by the choice of polymeric support, with regard to mechanical stability, swellablity, compatibility with a range of hydrophilic and/or hydrophobic solvents, and applicability to both batch wise and continuous flow reactors. The selection of possible supports introduced and tested over the years includes polyamides, polyamide composites, polyethylene-polystyrene films, cotton and other carbohydrates, controlled pore silica glass, polyethylene glycol-polystyrene (PEG-PS and Tentagel) graft resins.

Comparing all of these available polymeric supports the newly synthesized propoxylate function of hexanediol diacrylate gives considerable yield and purity. The outcome of a multistep solid-phase synthesis is dependent on the structure of the peptide to be prepared, the strategy followed, as well as the type of solid support employed. In order to ensure a proper solvation of the reactive species allowing fast and quantitative reactions, their polarity must also be compatible with those of the reagents and solvents used, as well as with these of the resin-bound growing peptide. Other styrene-based resins arising so many problems in SPPS, their mechanical stability and flexibility of the crosslinks are low compared with the newly developed system of propoxylate crosslinks. The polyethylene glycol based systems are showing high flexibility, but showing least mechanical stability cause steric problems in the entire system. Solid phase synthesis of peptides has witnessed dramatic progress since its inception. Various polymer supports, new linkers, protection schemes and coupling methods have since made the technique simple and almost foolproof. Sequence specific problems are some of the main problems in peptide synthesis. In solid phase peptide synthesis the sequence specific problem is present irrespective of resin type. Sequence specific problems have been found to be the result of the formation of β-sheet formation can bring additional cross-linking within the matrix; the synthesis of sequences favoring such secondary structures by SPPS will be difficult even if we use the supports having high swelling characteristics. Studies have shown that the formation of β-sheet structure is accompanied by a drastic decrease in swelling and solvation of the peptidyl resin. Thus, the main criteria in choosing a support for peptide synthesis is that it should be compatible with the peptide towards all the solvents used for the synthesis and capable of suppressing the β-sheet forming tendency of the growing peptide.

Thus there are several drawbacks and disadvantages in the prior art discussion of available resins, with this view in mind pointing out a styrene based polymer support having regulated flexibility, to avoid aggregation and β-sheet formation but still having swellablity in a wide range of solvents, a new polymeric support propoxylate function of hexanediol diacrylate crosslinked with polystyrene in bead form was synthesized. This polymer were found to be more easily swollen in both polar and non-polar solvents.

OBJECTS OF THE INVENTION

An object of this invention is to propose a novel polymer support for Solid phase peptides synthesis with high flexibility and mechanical stability.

Another object of this invention is to prepare a process for the preparation of the novel polymer support.

Further object of this invention is to prepare a polymeric support which is chemically and mechanically stable:
still further object of this invention is to prepare a polymeric support which is compatible to the peptide chains with optimum hydrophilic/hydrophobic balance.

Another object of this invention is to propose a polymer support which has high coupling efficiency and prevents β-sheet formation leads high yield and purity. Still another object of this invention is to propose a polymer support of uniform-swelling.

DETAILED DESCRIPTION OF THE INVENTION

According to this invention there is provided a novel polymer support for solid phase peptide synthesis comprising polystyrene backbone and propoxylate function of hexanedioldiacrylate crosslinks having optimum hydrophilic/hydrophobic balances.

Further, according to this invention there is also provided the polymer support shows effective swelling in polar and non-polar solvents.

Polymer support was synthesized by suspension polymerization of the respective amount of monomer and crosslinker. A definite volume of diluent is added. This organic mixture dispersed in polar dispersion medium containing 0.5–1.9% PVA as stabilizer. Mechanical agitation of this mixture resulted in the formation of small uniform droplets of the dispersed organic mixture. Radical initiator was added to the suspension mixture. The type and amount of the diluents played an important role in determining the size of the polymer. Smaller beads were obtained by increasing the aqueous to organic phase ratio of the suspension. Considerable speed is regulated for getting the uniform bead. When the speed increases the yield is found to be decreased. The indentation forces are resulting from the geometry of the vessel force the suspended mixture in towards the rotation stir blade. These result in a homogeneous shearing environment for the monomer droplets and create a uniform droplet size. The polymer bead of HDPA-PS is represented in FIG. 1. The synthesized polymer support was characterized by 1R, C NMR and SEM.

Chloromethyl groups were introduced to the polymer backbone by using CMME, an acronym for chloromethylmethylether, and Lewis acid catalyst. The reaction was controlled by altering the variants like time, temperature (35–60)° C., and amount of CMME. After introducing the chloromethyl group, it is converted to an amino group by hydrazinolysis. After attaching the amino group to the newly developed support HDPA-PS a suitable linker HMPB were introduced.

The swelling study of the newly developed resin is one of the parameters that determine the extent of variation in chemistry that occurs on microporous solid support. Swelling of the polymer allows effective diffusion of the solution phase reagents to polymer bound functional groups. Swelling of the polymer in various solvents was tested and compared with PS-DVB resin. There was no appreciable change in swelling characteristics between the functionalized and unfunctionalized resins suggesting that chloromethylation using CMME had not resulted in methylene bridge formation between the aromatic rings.

Mechanical and chemical stability of the crosslinked resin in different reagents and solvents was one of the prime requirements of an effective solid support for polypeptide synthesis. The polymer synthesized was extremely stable under all peptide synthetic conditions. The flexible site present in the crosslinker is found to be stable enough to withstand nucleophilic cleavage by strong bases and acids.

In SPPS covalent linkage between the growing peptide chain and the polymeric support plays an important role in determining the rate of release of final peptide from the support.

The newly developed system, HDPA-PS is used for the synthesis of difficult sequences of C-terminal ACP fragment and two more difficult sequences. In ACP and other fragments the HPLC profile gives a clear picture indicating that the system is perfectly suit for solid phase peptide synthesis. The polymer matrix is also used for the polypeptide synthesis of hepatitis-C antibodies. This also gives a good results portrait the efficiency of newly developed HDPA-PS. The purity was characterized by using HPLC and molecular mass was determined by MALDI-TOF MS technique. The present investigations revealing that, HDPA-PS is a suitable polymeric support for polypeptide synthesis of high yield and purity. The present system is studied and compared with Merrifield's DVB-PS and Sheppard resin. DVB-PS is rigid and its highly hydrophobic macromolecular network is incompatible with the growing peptide chain. This results in a negative influence, especially in polar organic solvents on various chemical reactions that take please between the reactants and the reactive centers of the polymer. This incompatibility can lead to the formation of truncated peptides due to the incomplete coupling and deprotection reactions and deletion sequences, due to the regrowth of the partially completed sequence. In order to overcome these difficulties HDPA-PS is very suit for solid phase peptide synthesis.

Example

For the preparation of 1% hexanediol propoxylate diacrylate crosslinked polystyrene, (0.30–0.35 ml) hexanediol propoxylate diacrylate+(11.29–11.34 ml) styrene are used. For 2% hexanediol propoxylate diacrylate crosslinked polystyrene, (0.60–0.69 ml) hexanediol propoxylate diacrylate+ (11.10–11.23 ml) styrene are used. In this way we can prepare (1–20mol%) HDPA-PS.

For the preparation of (1–20 mol%) HDPA-PS, in all cases we are taking initiator as benzoyl peroxide (300–600 mg) and diluent as toluene (4–10 ml) and polyvinyl alcohol (mol; weight below 1 lac) as suspension stabilizer. The yield obtained is in the range (3–6 g).

Experiment-1

The acronyms used below are defined as follows:
HDPA hexanediolpropoxylatediacrylate
HOBT 1-hydroxybenzotriazole
HBTU 2-(1H-benzotriazol-1-yl)-1,1,3,3-tetramethyluronium hexafluorophosphate
DIEA Diisopropylethylamine
ACP Acyl carrier protein fragment HDPA-PS-HMPB-OH, PS-DVB-HMPB-OH and Sheppard resins, used for the synthesis of the well known C-terminal region of ACP fragment (65–74), exemplified many of the sequence dependant problems which may be encountered during the course of solid-phase peptide synthesis. Many problems that have led to poor synthetic results could be traced back to the internal development of secondary structure which competes specifically with the desired amide bond formation. Segments that promote inter chain aggregation result in dramatic reduction in amino group accessibility. Consequently, this particular ACP sequence has become a standard test of peptide to asses the efficiency of a new polymeric support. In order to demonstrate the synthetic ability of HDPAPS this notoriously difficult sequence was synthesized side-by-side using HDPA-PS-HMIPB-OH, PS-DVB-HMPB-OH and Sheppard resins.

The respective resins were weighted in such as way that the quantity of glycine in a respective reaction vessel was the same. This was to make sure that the reaction conditions were uniform when the acylation was carried out with respective amino acid and coupling reagents. All coupling reactions were carried out using 4eq. excess of respective amino acid, HOBT, HBTU and DIEA. The total amount of these reagents required to incorporate an amino acid into these resins were weighed, dissolved in DMF and then distributed equally to each synthesizer. This further ensured identical coupling conditions. After synthesis, N-terminal Fmoc protection was removed from the corresponding resins under the same cleavage conditions. The ACP fragment obtained was dissolved in an equal volume of HPLC buffer A and purity was analyzed using a reverse-phase HPLC sephasil peptide C18 coloum. The study revealing that the average purity of ACP synthesized varied marginally in HDPA-PS compared with other two type resins. The yield obtained for PS-DVB is 40% and Sheppard resin is 68% and HDPA-PS have an yield 90%>under the same synthetic conditions.

Experiment 2

The efficiency of HDPA-PS-HMPB-OH support is demonstrated by synthesizing the peptide from the immunodominent region of hepatitis C viral pathogens to investigate viral immunity in human blood. The HDPA-PS-HMPB-OH support is studied comparatively with PS-DVB-HMPB-OH. The respective resins with same degree of C-terminal amino acid substitution were used for the study. In a typical coupling reaction total amino acid and coupling reagents required for both resins were weighed together, dissolved in DMF and then distributed equally to both resins. The coupling time gives was 40 min. Only a single coupling reaction was performed to incorporate a single amino acid. After synthesis, the peptide was cleaved from the support in 4 h by adding TFA scavenger mixture. The crude peptide obtained from the two resins was analyzed by HPLC. The peptide synthesized on HDPA-PS-HMPB-OH resin gave only one major peak, suggesting that the coupling and deprotection steps were driven to completion. The HPLC profiles of the peptide synthesized on PS-DVB-HMPB-OH resin resulted in several small peaks along with the major peak, suggesting the presence of deletion and truncated sequences. An octa peptide, corresponding to the sequence of the delicious peptide has been synthesized using HDPA-PS-HMPB were also obtained in pure form where characterized by HPLC.

We claim:

1. A novel polymer support for solid phase peptide synthesis comprising polystyrene backbone and propoxylate function of hexanedioldiacrylate crosslinks.

2. A polymer support as claimed in claim 1 wherein the said support suppresses β-sheet formation.

3. The polymer support as claimed in claim 1, wherein the polymer is HDPA-PS.

4. The polymer support as claimed in claim 1, swells in polar and non-polar solvents and withstands peptide synthetic conditions.

5. The polymer support as claimed in claim 1 wherein said polymer is prepared in bead form by suspension polymerization using styrene and said crosslinker, toluene as a diluent and benzoyl peroxide as an initiator and further comprising 0.5 to 1.9% of a stabilizer.

6. The polymer support as claimed in claim 5, wherein polymerization is carried out at 75–90° C. for 5–8 hours.

7. The polymer support as claimed in claim 5, wherein the size of the said polymer was controlled by speed of rotation.

8. The polymer support as claimed in claim 5, wherein a functionalization is carried out by chloromethylation for introducing a chloromethyl group to the said support, followed by a step of hydrazinolysis to convert the chloromethyl group to amino group.

9. The polymer support as claimed in claim 8, wherein chloromethylation is done by using chloromethylmethylether in presence of Lewis acid catalyst and a step of hydrazinolysis is conducted by using potassium phthalimide followed by hydrazine hydrate.

* * * * *